United States Patent
Mock-Knoblauch et al.

(10) Patent No.: US 7,727,948 B2
(45) Date of Patent: *Jun. 1, 2010

(54) MIXTURE, COMPRISING A SURFACTANT AND A COSURFACTANT THAT IS AN AMPHIPHILIC POLYMER

(75) Inventors: Cordula Mock-Knoblauch, Ludwigshafen (DE); Norbert Wagner, Mutterstadt (DE); Guenter Oetter, Frankenthal (DE); Ludwig Voelkel, Limburgerhof (DE); Bernhard Steinmetz, Limburgerhof (DE); Rainer Dyllick-Brenzinger, Speyer (DE); Joerg Schroeder, Weinheim (DE); Susanne Petrovic, Eppelheim (DE)

(73) Assignee: BASF SE, Ludwigshafen (DE)

( * ) Notice: Subject to any disclaimer, the term of this patent is extended or adjusted under 35 U.S.C. 154(b) by 408 days.

This patent is subject to a terminal disclaimer.

(21) Appl. No.: 10/557,600

(22) PCT Filed: May 21, 2004

(86) PCT No.: PCT/EP2004/005518

§ 371 (c)(1),
(2), (4) Date: Nov. 22, 2005

(87) PCT Pub. No.: WO2004/103542

PCT Pub. Date: Dec. 2, 2004

(65) Prior Publication Data

US 2007/0060495 A1 Mar. 15, 2007

(30) Foreign Application Priority Data

May 22, 2003 (DE) ............... 103 23 178

(51) Int. Cl.
- *C11D 3/37* (2006.01)
- *C11D 1/88* (2006.01)
- *A61K 8/06* (2006.01)
- *A61K 8/72* (2006.01)

(52) U.S. Cl. .......... 510/475; 510/276; 510/360; 510/361; 510/417; 510/433; 510/434; 510/476; 510/499; 424/486; 424/70.1; 424/70.19

(58) Field of Classification Search ......... 510/276, 510/360, 361, 417, 433, 434, 475, 476, 499; 424/486, 70.1, 70.19

See application file for complete search history.

(56) References Cited

U.S. PATENT DOCUMENTS 4,954,338 A * 9/1990 Mattox .............. 514/372

(Continued)

FOREIGN PATENT DOCUMENTS

DE 196 34 477 12/1997

(Continued)

OTHER PUBLICATIONS

Klier et al. "Properties and Applications of Microemulsions", Adv. Mater., vol. 12, No. 23, pp. 1751-1757 2000, Dec. 2000.

(Continued)

*Primary Examiner*—Brian P Mruk
(74) *Attorney, Agent, or Firm*—Oblon, Spivak, McClelland, Maier & Neustadt, L.L.P.

(57) ABSTRACT

A mixture of surfactant and co-surfactant which is an amphiphilic polymer with the formula:

$$A'-Y-[A]_m-X-([B]_n)_p-H. \quad (I)$$

19 Claims, 1 Drawing Sheet

U.S. PATENT DOCUMENTS

| | | | |
|---|---|---|---|
| 5,045,311 A * | 9/1991 | Pinter et al. | 514/75 |
| 5,932,630 A | 8/1999 | Kovacs et al. | |
| 6,133,218 A * | 10/2000 | Kerobo et al. | 510/365 |
| 6,506,485 B1 | 1/2003 | Pinnavaia et al. | |
| 6,835,701 B2 * | 12/2004 | Seipel et al. | 510/143 |
| 2003/0129151 A1 * | 7/2003 | Candau et al. | 424/59 |

FOREIGN PATENT DOCUMENTS

| | | |
|---|---|---|
| DE | 198 39 054 | 3/2000 |
| DE | 10117500 | * 10/2002 |

OTHER PUBLICATIONS

Eicke. "Mikroemulsionen -eine wissenschaftliche und anwendungstechnische Fundgrube?", SOEFW- Journal, vol. 118, pp. 311-315 1992, May 1992 (Not Translated).

* cited by examiner

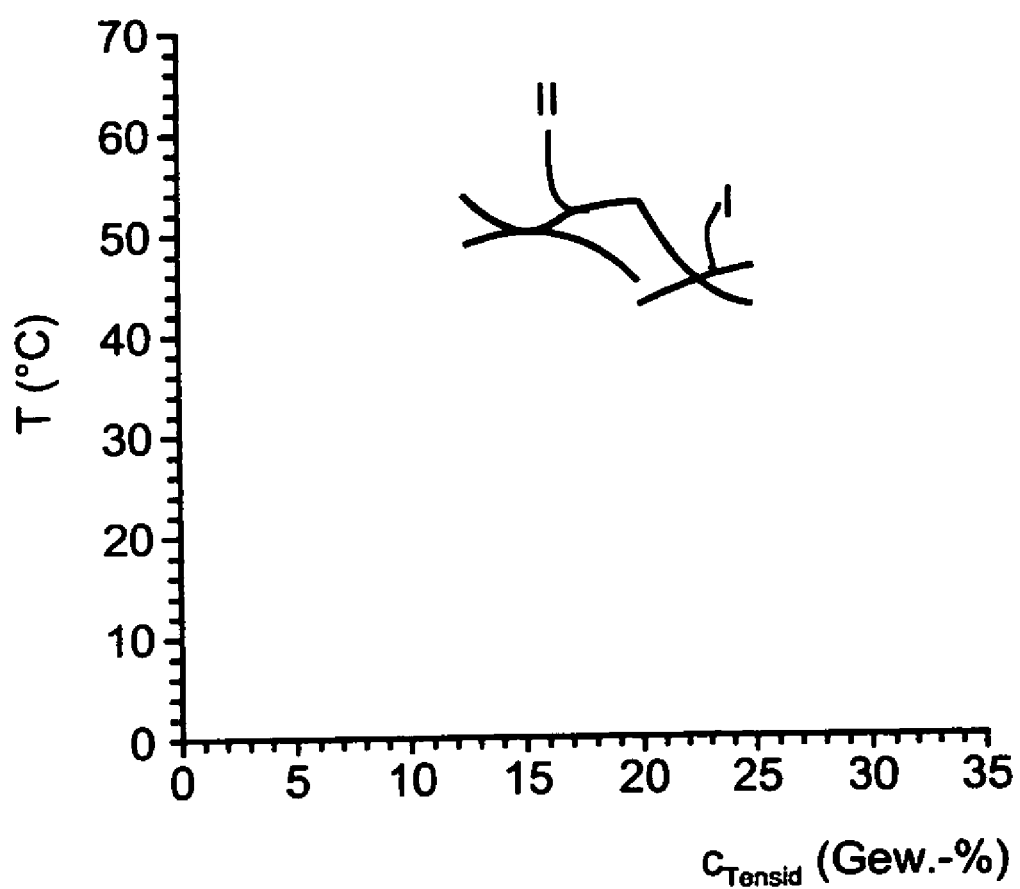

MIXTURE, COMPRISING A SURFACTANT AND A COSURFACTANT THAT IS AN AMPHIPHILIC POLYMER

The invention relates to a mixture comprising a surfactant and a cosurfactant, to a use of a mixture for stabilizing emulsions, to a process for the preparation of an amphiphilic polymer, to a microemulsion comprising a surfactant and a cosurfactant, to a use of a mixture or of a microemulsion, and to detergents, cleaners, disinfectants, wetting agents, coatings, adhesives, leather degreasing compositions, humectants or textile treatment compositions or pharmaceutical, crop protection or cosmetic formulation, in particular sunscreen, skincare or hair styling compositions, shower gels, shampoos, bath additives or scent oils.

Surfactants are substances which reduce the interfacial tension between liquid phases which are not miscible with one another, a polar phase, often water and a nonpolar, organic phase, and thus increase their mutual solubility. Surfactants have a characteristic structure and have at least one hydrophilic and one hydrophobic structural unit. This structure is also referred to as amphiphilic.

Surfactants are particularly relevant substances in ecological terms and their environmental compatibility must be ensured. As well as good degradability of surfactant residues in waste waters, it is therefore particularly important to reduce the amounts of surfactant used as far as possible without impairing their effectiveness, i.e. to increase the efficiency of the surfactants. In this connection, surfactant efficiency is usually used to refer to the amount of surfactant which is required in order to achieve a certain effect, for example in order to solubilize the fraction of nonpolar phase in the polar phase, or vice versa, or in order to reduce to the greatest possible extent the surface tension at the lowest possible concentration.

Customary conventional emulsions can comprise oil and water phases in very different fractions by volume. They have one continuous phase and one disperse phase, which is present as very small spheres which have been stabilized by coating with surfactants, in the continuous phase. Depending on the nature of the continuous phase, the emulsions are described as oil-in-water or water-in-oil. These emulsions are kinetically stable in the ideal case, i.e. they are retained even for a prolonged period, but not indefinitely. During temperature fluctuations in particular, they may have a tendency toward phase separation as a result of sedimentation, creaming, thickening or flocculation.

So-called microemulsions are thermodynamically stable, fluid, optically clear formulations of two immiscible liquids, such as oil and water. Microemulsions arise when a surfactant, or more frequently a mixture of a surfactant and a cosurfactant, reduces the oil/water interfacial tension to extremely low values, often in the range $10^{-3}$ to $10^{-9}$, preferably $10^{-4}$ to $10^{-6}$ N/m, such that the two insoluble phases remain dispersed by themselves in a homogeneous manner as a result of the thermal agitation. Microemulsions often have bicontinuous structures with equilibrium regions, so-called subphases in the order of magnitude from 100 to 1000 Angströms (cf. Advanced Materials, 2000, 12, No. 23, pages 1751 et seq.).

Bicontinuous microemulsions comprise two phases, a water phase and an oil phase, in the form of extended adjoining and intertwined domains at whose interface stabilizing interface-active surfactants are concentrated in a monomolecular layer. Bicontinuous micro emulsions form very readily, usually spontaneously due to the very low interfacial tension, when the individual components, water, oil and a suitable interface-active system, are mixed. Since the domains have only very small extensions in the order of magnitude of nanometers in at least one dimension, the microemulsions appear visually transparent and are thermodynamically, i.e. indefinitely, stable in a certain temperature range depending on the interface-active system used.

Bicontinuous microemulsions are described, for example, in the article "Mikroemulsionen—eine wissenschaftliche und anwendungstechnische Fundgrube?" [Microemulsions, a scientific and performance treasure trove?] by H.-F. Eicke in SÖFW-Journal 118 (1992), pages 311 to 314.

To achieve the required low interfacial tension at the phase boundaries, the microemulsions comprise special amphiphiles, i.e. interface-active agents, and electrolytes often dissolved in their aqueous phase and optionally further auxiliaries. Electrolytes are primarily added when the amphiphiles are partly or exclusively ionic surfactants.

It is known from DE-A 198 39 054 to increase the efficiency of surfactants by adding additives, the additives used being AB block copolymers with a water-soluble block A and a water-insoluble block B. The blocks A and B can here have molecular weights between 500 and 60 000 g/mol. As block A, preference is given to using a polyethylene oxide block, but generally all water-soluble blocks which form an amphiphile in combination with block B. For block B, polymers of a single monomer or a monomer mixture are described.

However, the described block copolymers have the disadvantage, in particular, that they are obtainable by preparation processes which are suitable for a laboratory scale, but not for large scale use. Said specification refers for the preparation process to DE-A 196 34 477, in which the polymerization using organo-alkali metals is described, i.e. a preparation method unsuitable for large-scale use.

It is an object of the present invention to provide substances which can be used as cosurfactants for increasing the efficiency of surfactants in emulsions, in particular in microemulsions, and which can be obtained in an economically advantageous manner on the basis of large-scale starting substances and by reaction pathways which can be realized on an industrial scale. In particular, the aim is to achieve an increase in the efficiency of surfactants in bicontinuous microemulsions.

We have found that this object is achieved by a mixture comprising a surfactant and a cosurfactant, wherein the cosurfactant used is an amphiphilic polymer with the structural formula

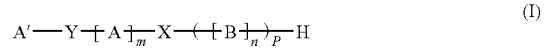
(I)

in which

A' is an unbranched or branched alkyl, cycloalkyl, aryl or aralkyl radical having 1 to 60 carbon atoms,
Y is O or S,
A is a structural unit with the formula

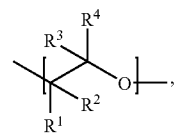

in which

R¹, R², R³ and R⁴ independently of one another, are the substituents hydrogen, methyl, ethyl, n-propyl, isopropyl, octyl or phenyl, with the restriction that at most three of the substituents R¹, R², R³ and R⁴ are hydrogen, m is a running number in the range from 10 to 300, X is a structural unit with the formula

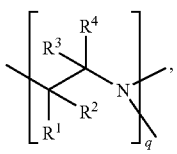

in which the substituents

R¹, R², R³ and R⁴ independently of one another, are each hydrogen, methyl, ethyl, n-propyl, isopropyl, octyl or phenyl, q=0 or q=1, B is a monomeric subunit based on ethylene oxide or a mixture of ethylene oxide and propylene oxide, n is a running number in the range from 20 to 500 and p=q+1.

It has surprisingly been found that amphiphilic polymers with the structure defined above are particularly suitable as cosurfactants in that they increase the efficiency of surfactants and are obtainable from large-scale and thus inexpensively obtainable substances by industrial reaction pathways. The amphiphilic polymers according to the invention are usually technical-grade mixtures of substances with a more or less broad molecular weight distribution.

The structural formula thus covers both linear structures, when q=0, and structures branched in y form, when q=1.

The structural unit A'-Y is a hydrophobic component of the cosurfactant, and more specifically a monofunctional unbranched or branched alcohol or thiol radical derived from the group of $C_1$- to $C_{60}$-alkyl, cycloalkyl, aryl or aralkyl alcohols or thiols. Preference is given to branched or unbranched alcohols or thiols with 8 to 30 carbon atoms per alcohol or thiol radical.

Although in principle all shorter-chain aliphatic monohydroxy alcohols having 1 to 5 carbon atoms per molecule can also be used as starter alcohols A'-OH, preference is given to monofunctional aliphatic alcohols having 6 to 18 carbon atoms per molecule, and particular preference is given to monofunctional aliphatic alcohols having 8 to 15 carbon atoms per molecule.

Alcohols which are suitable according to the invention are, in particular, octanol, 2-ethylhexanol, nonanol, decanol, undecanol, dodecanol, 2-butyloctanol, tridecanol, tetradecanol, pentadecanol, isooctanol, isononanol, isodecanol, isoundecanol, isododecanol, isotridecanol, isotetradecanol, isopentadecanol, preferably isodecanol, 2-propylheptanol, tridecanol, isotridecanol or mixtures of $C_{13}$- to $C_{15}$-alcohols or mixtures of 2-propylheptanol with structurally isomeric $C_{10}$-alcohols. Oxo alcohols, as are customarily obtained by hydroformulation of linear or branched olefins having 4 to 29 carbon atoms, which can be prepared, for example, by oligomerization of ethene, propene, 1-butene, isomeric butene mixtures or from mixtures of the abovementioned alkenes, or derive from alcohols, as are obtained starting from olefins having 5 to 30 carbon atoms either by ozonolysis and subsequent reduction or by epoxidation and subsequent hydrolysis or by halogenation with chlorine or bromine and subsequent alkaline hydrolysis.

For example, the alcohols used as starter compound according to the invention may be Guerbet alcohols, in particular ethylhexanol, propylheptanol, butyloctanol. Thus, in a particularly preferred embodiment, the present invention also provides a process where the starter compound is a Guerbet alcohol.

The alcohols used as starter compound may also be mixtures of different isomers.

These mixtures can be derived from the abovementioned alcohols or be produced during their preparation, for example crude products and individual fractions, as are produced during the distillative work-up of the crude products. Examples of suitable mixtures are so-called oxo oils or oxo oil fractions, as are often produced during the preparation of oxo alcohols.

Advantageously, the starter alcohol A'-OH which may be used is an alcohol mixture which is obtained by trimerization of butene and subsequent hydroformylation and hydrogenation, and is referred to as tridecanol N.

Propylheptanol, for example, can be obtained starting from valderaldehyde by aldol condensation and subsequent hydrogenation. The preparation of valeraldehyde and the corresponding isomers takes place by hydroformylation of butene, as described, for example, in U.S. Pat. No. 4,287,370; Beilstein E IV 1, 32 68, Ullmanns Encyclopedia of Industrial Chemistry, 5th edition, volume A1, pages 323 and 328 f. The subsquent aldol condensation is described, for example, in U.S. Pat. No. 5,434,313 in Römpp, Chemie Lexikon, 9th edition, key word "Aldol addition", page 91. The hydrogenation of the aldol condensation product follows general hydrogenation conditions.

Furthermore, 2-propylheptanol can be prepared by condensation of 1-pentanol (as the mixture of the corresponding 1-methylbutanols) in the presence of KOH at elevated temperatures, see, for example, Marcel Guerbet, C. R. Acad Sci Paris 128, 511, 1002 (1899). Furthermore, reference is made to Römpp, Chemie Lexikon, 9th edition, Georg Thieme Verlag Stuttgart, and the citations given therein, and also Tetrahedron, Vol. 23, pages 1723 to 1733.

In addition, alcohols which arise from an addition of acetone onto aldehydes with subsequent hydrogenation, as described in DE-A 100 35 617, are also suitable. Also suitable are paraffin oxidation products which essentially represent secondary alcohols (for example from $C_{12/14}$-paraffin mixtures or $C_{10}$- to $C_{16}$-paraffin mixtures). Suitable alcohols are also, for example, secondary alcohols which are obtained by acidic addition of water onto olefins or by free-radical or other oxidation of olefins.

By means of the processes described above, a large number of commercial products are also obtainable, which are often in the form of isomer mixtures and are available at low cost. Examples which may be mentioned are the product of the reaction of 2-ethylhexanal with acetone or methyl ethyl ketone and final hydrogenation, the product of the reaction of $C_{13/15}$-aldehyde with acetone or methyl ethyl ketone, the product of the reaction of an isomer mixture of different $C_{13}$-aldehydes, of so-called isotridecanal with acetone or methyl ethyl ketone. Examples of starter alcohols which are obtainable by the addition of water onto the α-olefine are 2-decanol, 2-dodecanol, 2-tetradecanol or 2-hexadecanol.

Suitable starter alcohols A'-OH are also alicyclic and aromatic hydroxy compounds, preferably compounds of the formulae

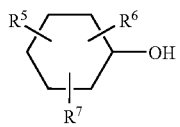 and 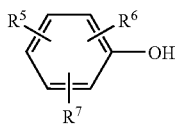

in which $R^5$, $R^6$ and $R^7$, independently of one another, are hydrogen or $C_1$-$C_{30}$-alkyl.

Preferred alicyclic and aromatic hydroxy compounds are cyclohexanol, phenol, the cresol isomers, isobutylphenol, isobutylcresol, diisobutylphenol, diisobutylcresol, tert-butylphenol, tert-butylcresol, di-tert-butylphenol, di-tert-butylcresol, isooctylphenol, diisooctylphenol, isononylphenol, diisononylphenol, isododecylphenol, diisododecylphenol and mixtures thereof.

The hydrophobic structural unit A is preferably formed from one or more of the following monomers: propene oxide, 1-butene oxide, 2,3-butene oxide, 2-methyl-1,2-propene oxide (isobutene oxide), 1-pentene oxide, 2,3-pentene oxide, 2-methyl-1,2-butene oxide, 3-methyl-1,2-butene oxide, 2,3-hexene oxide, 3,4-hexene oxide, 2-methyl-1,2-pentene oxide, 2-ethyl-1,2-butene oxide, 3-methyl-1,2-pentene oxide, 4-methyl-1,2-pentene oxide, decene oxide, 4-methyl-1,2-pentene oxide, styrene oxide or from mixtures thereof. These include preferably also mixtures obtainable by oxidation of industrially obtainable olefin streams, which may comprise further alkylene oxides different from those mentioned above and/or olefins and/or inert substances (alkanes) not included by the oxidation.

The running number m, which refers to the number of repeat structural units A, preferably assumes a value in the range from 50 to 250, in particular from 60 to 160.

The structural unit X, comprising an amino group, can be incorporated into the amphiphilic polymer as branching point.

The structural unit $[B]_n$ is a hydrophilic component of the cosurfactant, formed from repeat ethylene oxide or ethylene oxide/propylene oxide units. Here, B is a monomeric subunit based on ethylene oxide or on a mixture of ethylene oxide (EO) and propylene oxide (PO). The structural unit $[B]_n$ may be a random copolymer, a gradient copolymer, an alternating or a block copolymer of EO and PO.

The polymer structure can comprise a single hydrophilic component $[B]_n$ or else, via the branching point on the nitrogen atom, two hydrophilic components $[B]_n$.

The running number n, which refers to the number of repeat structural units B, preferably assumes a value in the range between 50 and 300.

Advantageously, B may be an ethylene oxide/propylene oxide mixture containing 0 to 50% of propylene oxide, preferably containing 5 to 20% of propylene oxide.

As well as the cosurfactants described above, the mixture according to the invention comprises a surfactant. This may be a mixture of surfactants. In principle, any surfactant from any of the known surfactant groups, in particular ionic or nonionic surfactants, and also mixtures of ionic or nonionic surfactants, can be used.

Depending on the field of use of the mixtures according to the invention, suitable surfactants are, for example, all classical cleaning surfactants, or food-approved surfactants, such as Tweens® or Spans®. As far as the surfactant classes are concerned, nonionic, anionic, cationic, amphoteric surfactants are suitable; in particular also polymer surfactants, peptide surfactants, silicone surfactants, amino acid-based surfactants, sugar surfactants, fat-based surfactants, gemini surfactants, amine oxides, amidoamine oxides, alkylbetaines, ether carboxylates, amphoacetates, alkyl sulfates or sulfosuccinates.

The proportion of the cosurfactant, based on the surfactant, is preferably in the range from 0.01 to 99.99%, in particular between 1 and 50%, particularly preferably between 5 and 25%.

Suitable anionic surfactants are, for example, fatty alcohol sulfates or fatty alcohols having 8 to 22, preferably 10 to 18, carbon atoms, for example $C_9$- to $C_{11}$-alcohol sulfates, $C_{12}$- to $C_{13}$-alcohol sulfates, cetyl sulfate, myristyl sulfate, palmityl sulfate, stearyl sulfate and tallow fatty alcohol sulfate.

Further suitable anionic surfactants are sulfated ethoxylated $C_8$- to $C_{22}$-alcohols (alkyl ether sulfates) or soluble salts thereof. Compounds of this type are prepared, for example, by firstly alkoxylating a $C_8$- to $C_{22}$-, preferably a $C_{10}$- to $C_{18}$-, alcohol, for example a fatty alcohol, and then sulfating the alkoxylation product. For the alkoxylation, preference is given to using ethylene oxide, employing 2 to 50, preferably 3 to 20, mol of ethylene oxide per mole of fatty alcohol. The alkoxylation of the alcohols can, however, also be carried out with propylene oxide on its own and optionally butylene oxide. Also suitable are those alkoxylated $C_8$- to $C_{22}$-alcohols which comprise ethylene oxide and propylene oxide or ethylene oxide and butylene oxide. The alkoxylated $C_8$- or to $C_{22}$-alcohols can comprise the ethylene oxide, propylene oxide and butylene oxide units in the form of blocks or in random distribution.

Also suitable are alkanesulfonates, such as $C_8$- to $C_{24}$-, preferably $C_{10}$- to $C_{18}$-, alkanesulfonates, and soaps, such as Na or K salts of $C_8$- to $C_{24}$-carboxylic acids.

Further suitable anionic surfactants are N-acylsarcosinates with aliphatic saturated or unsaturated $C_8$- to $C_{25}$-acyl radicals, preferably $C_{10}$- to $C_{20}$-acyl radicals, for example N-oleoylsarcosinate.

In addition, the mixtures according to the invention can comprise $C_{10}$- to $C_{13}$-linear and/or slightly branched alkylbenzenesulfonates (LAS).

The anionic surfactants are added to the mixture, preferably in the form of salts. Suitable cations in these salts are alkali metal salts, such as sodium, potassium and lithium and ammonium salts, such as, for example hydroxyethylammonium, di(hydroxyethyl)ammonium and tri(hydroxyethyl)ammonium salts.

Suitable nonionic surfactants are, in particular:
  alkoxylated $C_8$- to $C_{22}$-alcohols such as fatty alcohol alkoxylates or oxo alcohol alkoxylates. These may be alkoxylated with ethylene oxide, propylene oxide and/or butylene oxide. Surfactants which may be used here are all alkoxylated alcohols which comprise at least two added molecules of one of the alkylene oxides specified above. In this connection, block polymers of ethylene oxide, propylene oxide and/or butylene oxide are suitable or addition products which comprise said alkylene oxides in random distribution. The nonionic surfactants comprise, per mole of alcohol, generally 2 to 50, preferably 3 to 20, mol of at least one alkylene oxide. These preferably comprise ethylene oxide as alkylene oxide. The alcohols preferably have 10 to 18 carbon atoms. Depending on the nature of the alkoxylation catalyst used in the preparation, the alkoxylates have a broad or narrow alkylene oxide homolog distribution;
  alkylphenol alkoxylates, such as alkylphenol ethoxylates with $C_6$- to $C_{14}$-alkyl chains and 5 to 30 alkylene oxide units;

alkyl polyglucosides having 8 to 22, preferably 10 to 18, carbon atoms in the alkyl chain and generally 1 to 20, preferably 1.1 to 5, glucoside units sorbitan alkanoates, also alkoxylated;

N-alkylglucamides, fatty acid alkoxylates, fatty acid amine alkoxylates, fatty acid amide alkoxylates, fatty acid alkanolamide alkoxylates, alkoxylated, block copolymers of ethylene oxide, propylene oxide and/or butylene oxide, polyisobutene ethoxylates, polyisobutene-maleic anhydride derivatives, monoglycerides, also alkoxylated, and bisglycerides.

Particularly suitable nonionic surfactants are alkyl alkoxylates or mixtures of alkyl alkoxylates, as are described, for example, in DE-A 102 43 363, DE-A 102 43 361, DE-A 102 43 360, DE-A 102 43 365, DE-A 102 43 366, DE-A 102 43 362 or in DE-A 43 25 237. These are alkoxylation products which have been obtained by reacting alkanols with alkylene oxides in the presence of alkoxylation catalysts, or are mixtures of alkoxylation products. Particularly suitable starter alcohols are the so-called Guerbet alcohols, in particular ethylhexanol, propylheptanol and butyloctanol. Particular preference is given to propylheptanol. Preferred alkylene oxides are propylene oxide and ethylene oxide, with alkyl alkoxylates with a direct bond of a preferably short polypropylene oxide block to the starter molecular, as are described, for example, in DE-A 102 43 365, being preferred in particular on the basis of their low residual alcohol content and their good biodegradability.

Alkoxylation catalysts which may be used are bases, for example alkali metal hydroxides or alkali metal alkoxides, but also Lewis acids, for example $BF_3$, $SbCl_5$, $SnCl_4 \times 2H_2O$, $BF_3 \times H_3BO_4$, or $BF_3$ dietherate. Particularly suitable alkoxylation catalysts are double hydroxide clays, such as hydrotalcite, which may, in particular, be modified with additives, as described in DE-A 43 25 237.

Depending on the choice of alkoxylation catalyst, specific properties of the alkoxylates result in each case, in particular with regard to the distribution of the degree of alkoxylation. For example, if the last-mentioned double-hydroxide clays are used, the alkoxylation products obtained have a narrow molecular weight distribution or homolog distribution and are particularly suitable for use in the mixtures according to the invention with cosurfactants.

The advantageous properties described above, in particular with regard to the degree of alkoxylation, are also achieved through the use of double metal cyanide (DMC) compounds, as are described, for example, in DE-A 102 43 361 as alkoxylation catalysts.

The invention also provides a process for the preparation of an amphiphilic polymer with the structural formula (I)

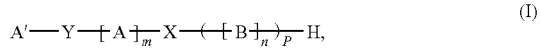

(I)

which comprises reacting a monohydric unbranched or branched alcohol or a corresponding thiol with a monomer which forms the structural unit

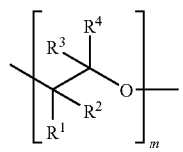

and reacting
the terminal OH group directly with ethylene oxide or a mixture of ethylene oxide and propylene oxide or
the terminal OH group firstly to give a primary or secondary amine and then with ethylene oxide or a mixture of ethylene oxide and propylene oxide.

The process according to the invention is based on starting materials which are accessible on a large scale and which lead to the desired cosurfactant structures by reactions which can be realized simply on a large scale.

Alkoxylation catalysts which may be used are bases, for example alkali metal hydroxides or alkali metal alkoxides, but also Lewis acids, for example $BF_3$, $SbCl_5$, $SnCl_4 \times 2H_2O$, $BF_3 \times H_3BO_4$, or $BF_3$ dietherate. Particularly suitable alkoxylation catalysts are double-hydroxide clays, such as hydrotalcite, which may, in particular, be modified with additives, as described in DE-A 43 25 237.

Depending on the choice of alkoxylation catalyst, specific properties of the alkoxylates result in each case, in particular with regard to the distribution of the degree of alkoxylation. For example, if the last-mentioned double-hydroxide clays are used, the alkoxylation products obtained have a narrow molecular weight distribution or homolog distribution and are particularly suitable as cosurfactants for use in the mixtures according to the invention.

The advantageous properties described above, in particular with regard to the degree of alkoxylation, are also achieved through the use of double-metal cyanide (DMC) compounds, as are described, for example, in DE-A 102 43 361 as alkoxylation catalysts.

The invention also provides for the use of a mixture comprising a surfactant and an above-described cosurfactant for stabilizing emulsions, in particular oil/water emulsions, water/oil emulsions, microemulsions or multiple emulsions such as oil/water/oil emulsions or water/oil/water emulsions. In the present context, stabilization means that the efficiency of surfactants is increased through the addition of cosurfactants, i.e. the solubilization of a defined oil/water mixture is made possible under defined conditions with a relatively small amount of surfactant.

The above-described cosurfactants are particularly preferably suitable for stabilizing microemulsions, i.e. for shifting the so-called X point, which represents the lowest concentration of surfactant at a given temperature from which the thermodynamic state of the microemulsion, i.e. the single-phase state when examined microscopically, arises, to lower surfactant concentrations.

The mixtures according to the invention can in principle be used in all areas where emulsions play a role, for example in the fields of application listed in DE-A 101 18 480 for mixtures comprising a surfactant and an AB block copolymer as additive (cosurfactant), which also comprise additives whose efficiency can be increased by the surfactant/additive system: for example as crop restoration, growth or crop protection compositions, products with microbiocidal active ingredients, products with positively or negatively acting microorganisms, in particular with a content of enzymes, cleaners and/or care compositions for the home and for commercial purposes, disinfectants, hair, bodycare or cleansing compositions, automobile cleaning, care and/or preservation compositions, textile treatment compositions, leather and/or fur care compositions, as paints, coatings, medicaments, construction aids, toothpastes or mouthwashes.

Synergistic effects, as are described in DE-A 101 18 480 for the surfactant/AB block copolymer system in combination with additional biocides, microorganisms and/or any other active ingredients, are achieved correspondingly for systems comprising the mixtures according to the invention comprising a surfactant and a cosurfactant, and corresponding additives, in particular biocides, microorganisms and/or any other active ingredients.

The invention also provides a microemulsion comprising a surfactant and a cosurfactant, wherein the cosurfactant used is an amphiphilic polymer with the structural formula

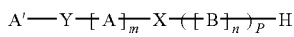  (I)

in which
A' is an unbranched or branched alkyl, cycloalkyl, aryl or aralkyl radical having 1 to 60 carbon atoms,
Y is O or S,
A is a structural unit with the formula

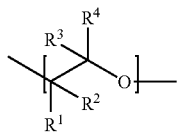

in which
$R^1$, $R^2$, $R^3$ and $R^4$ independently of one another, are the substituents
hydrogen, methyl, ethyl, n-propyl, isopropyl, octyl or phenyl, with the restriction that at least two and at most three of the substituents $R^1$, $R^2$, $R^3$ and $R^4$ are hydrogen,
m is a running number in the range from 10 to 300,
X is a structural unit with the formula

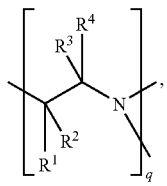

in which the substituents
$R^1$, $R^2$, $R^3$ and $R^4$ independently of one another, are the substituents hydrogen, methyl, ethyl, n-propyl, isopropyl, octyl or phenyl,
q=0 or q=1,
B is a monomeric subunit based on ethylene oxide or a mixture of ethylene oxide and propylene oxide,
n is a running number in the range from 20 to 500 and
p=q+1.

The microemulsion is in principle not restricted with regard to the surfactant or surfactant mixture which can be used. Preferred surfactants are described above.

As well as a surfactant and a cosurfactant as defined above, the microemulsion comprises a polar phase, generally water, and a nonpolar phase, generally one or more hydrocarbons.

Preference is given to a microemulsion comprising a cosurfactant, in which A'-Y is an aliphatic, alicyclic, aromatic or aliphatic-aromatic, monohydroxyalcohol or thiol radical having 8 to 30 carbon atoms per molecule.

Preferably, the microemulsion comprises a cosurfactant whose structural unit A is formed from one or more of the following monomers: propylene oxide, n-butylene oxide, isobutylene oxide, n-pentene oxide, decene oxide, styrene oxide or from a mixture of oxides of industrially available raffinate streams.

Preferably, in the cosurfactants which form the microemulsion, the running number m assumes a value in the range from 50 to 250, in particular from 60 to 160.

Further preferably, in the cosurfactants which form the microemulsion, the running number n assumes a value in the range from 50 to 300.

In the cosurfactants which form the microemulsion, B is preferably an ethylene oxide/propylene oxide mixture containing 0 to 50%, particularly preferably containing 5 to 20%, of propylene oxide.

The mixtures according to the invention are optimally suitable for the uptake and release of hydrophobic substances, in particular the use as detergent, emulsifier, foam regulator, wetting agent for hard surfaces or as reaction medium for organic, inorganic, bioorganic or photochemical reactions.

Preference is given to use in detergents, surfactant formulations for the cleaning of hard surfaces, humectants, cosmetic, pharmaceutical and crop protection formulations, paints, coatings, adhesives, leather degreasing compositions, formulations for the textile industry, fiber processing, metal processing, food industry, water treatment, paper industry, fermentation, mineral processing, fire protection or in emulsion polymerizations.

The invention further provides detergents, cleaners, disinfectants, wetting agents, coatings, adhesives, leather degreasing compositions, humectants or textile treatment compositions or pharmaceutical, food, crop protection or cosmetic formulation, in particular sunscreen, skincare or hair styling compositions, shower gels, shampoos, bath additives or scent oils comprising, as well as customary ingredients, a mixture comprising a surfactant and a cosurfactant as described above or a microemulsion comprising a surfactant and a cosurfactant.

The use of the mixtures according to the invention is particularly suitable in preparations for use in cosmetics, pharmacy and in the food sector, comprising at least one retinoid, at least one water-soluble antioxidant and at least one oil-soluble oxidant, as are described in the German patent application DE 102 337 40.3, which was unpublished at the priority date of the present invention and the disclosure content of which is hereby incorporated into the present patent application in its entirety by reference. These are cosmetic and dermatological or pharmaceutical preparations which are generally constructed on the basis of a carrier which comprises at least one oil phase. Accordingly, oils, creams, pastes or grease free gels or, preferably, emulsions are suitable.

The specified preparations comprise, per part by weight of retinoid, at least one part by weight of one or more water-soluble antioxidants and 0.1 to 100 parts by weight of one or more oil-soluble antioxidants, where the content of one or more water-soluble antioxidants is in the range from 0.05 to 0.8% by weight, based on the total amount of the preparations.

Retinoids are understood as being vitamin A alcohol (retinol) and its derivatives, such as vitamin A aldehyde (retinal), vitamin A acid (retinoic acid) and vitamin A esters, such as retinyl acetate and retinyl palmitate. The term retinoic acid comprises here both all-trans retinoic acid and also 13-cis retinoic acid. The terms retinol and retinal preferably comprise the all-trans compounds. A preferred retinoid used for the preparations according to the invention is all-trans-retinol.

Water-soluble antioxidants are understood as meaning, inter alia, ascorbic acid, sodium sulfite, sodium metabisulfite, sodium bisulfite, sodium thiosulfite, sodium formaldehyde sulfoxylate, isoascorbic acid, thioglycerol, thiosorbitol, thiourea, thioglycolic acid, cysteine hydrochloride, 1,4-diazobicyclo(2,2,2)octane or mixtures thereof.

Preferred water-soluble antioxidants are ascorbic acid (L-ascorbic acid) and isoascorbic acid (D-ascorbic acid), particularly preferably L-ascorbic acid.

The L-ascorbic acid which is particularly preferably used may be the free acid or else salts thereof. Examples of salts of L-ascorbic acid are alkali metal or alkaline earth metal salts of L-ascorbic acid, such as sodium L-ascorbate, potassium L-ascorbate or calcium L-ascorbate, but also salts of L-ascorbic acid with an organic amine compound, such as choline ascorbate or L-carnitin ascorbate. Very particular preference is given to using free L-ascorbic acid or sodium L-ascorbate. The same is true for the use of D-ascorbic acid.

Oil-soluble antioxidants are intended to mean, inter alia, butylated hydroxytoluene (BHT), ascorbyl palmitate, butylated hydroxyanisole, α-tocopherol, phenyl-α-naphthylamine or mixtures thereof.

A preferred oil-soluble antioxidant is α-tocopherol, which may here either be (R,R,R)- or (all-rac)-α-tocopherol.

With regard to the cosmetic or pharmaceutical preparations, customary auxiliaries are suitable, for example, coemulsifiers, fats and waxes, stabilizers, thickeners, biogenic active ingredients, film formers, fragrances, dyes, pearlizing agents, preservatives, pigments, electrolytes (for example magnesium sulfate) and pH regulators. Suitable coemulsifiers are preferably known W/O and also O/W emulsifiers, such as, for example, polyglycerol esters, sorbitan esters or partially esterified glycerides. Typical examples of fats are glycerides; waxes to be mentioned are, inter alia, beeswax, paraffin wax or microwax, if appropriate in combination with hydrophilic waxes. Stabilizers which can be used are metal salts of fatty acids, such as, for example, magnesium stearate, aluminum stearate and/or zinc stearate. Suitable thickeners are, for example, crosslinked polyacrylic acids and derivatives thereof, polysaccharides, in particular xanthan gum, guar guar, agar agar, alginates and tyloses, carboxymethylcellulose and hydroxyethylcellulose, and also fatty alcohols, monoglycerides and fatty acids, polyacrylates, polyvinyl alcohol and polyvinylpyrrolidone. Biogenic active ingredients are understood as meaning, for example, plant extracts, protein hydrolysates and vitamin complexes. Customary film formers are, for example, hydrocolloids, such as chitosan, microcrystalline chitosan or quatemized chitosan, polyvinylpyrrolidone, vinylpyrrolidone-vinyl acetate copolymers, polymers of the acrylic acid series, quaternary cellulose derivatives and similar compounds. Suitable preservatives are, for example, formaldehyde solution, p-hydroxybenzoate or sorbic acid. Suitable pearlizing agents are, for example, glycol distearic esters, such as ethylene glycol distearate, but also fatty acids and fatty acid monoglycol esters. Dyes which can be used are the substances approved and suitable for cosmetic purposes, as are listed, for example in the publication "Kosmetische Fäbemittel [Cosmetic Colorants]" from the Dyes Commission of the German Research Society, published by Verlag Chemie, Weinheim 1984. These dyes are usually used in concentrations of from 0.001 to 0.1% by weight, based on the total mixture.

The mixtures according to the invention can also advantageously be used in cosmetic or dermatological preparations comprising at least one UV filter, particularly preferably in cosmetic or dermatological preparations comprising, as UV-B filter, 2,4,6-trianilino-p-(carbo-2'-ethylhexyl-1'-oxy)-1,3,5-triazine, which is marketed by BASF AG under the trade name Uvinul® T150 and, as UV-A filter, N,N-diethylaminohydroxybenzoyl N-hexylbenzoate, which is marketed by BASF AG under the trade name Uvinul® A Plus.

mixtures according to the invention can particularly advantageously be present in cosmetic or dermatological preparations, as are described in the German patent application DE 102 00 400 7885.8, which was unpublished at the priority date of the present invention and which is hereby incorporated in its entirety into the disclosure content of the present patent application by reference.

The specified patent application describes a combination of Uvinul® T150, Uvinul® A Plus together with zinc oxide and/or titanium dioxide, where, in addition, UV-A and UV-B filter substances from the following table may be present:

| No. | Substance | CAS No. (= acid) |
|---|---|---|
| 1 | 4-Aminobenzoic acid | 150-13-0 |
| 2 | 3-(4'Trimethylammoniumbenzylidenebornan-2-one methyl sulfate | 52793-97-2 |
| 3 | 3,3,5-Trimethylcyclohexyl salicylate (homosalate) | 118-56-9 |
| 4 | 2-Hydroxy-4-methoxybenzophenone (oxybenzone) | 131-57-7 |
| 5 | 2-Phenylbenzimidazole-5-sulfonic acid and its potassium, sodium and triethanolamine salts | 27503-81-7 |
| 6 | 3,3'-(1,4-Phenylenedimethine)bis (7,7-dimethyl-2-oxobicyclo[2.2.1]heptane-1-methanesulfone | 90457-82-2 |
| 7 | Polyethoxyethyl 4-bis(polyethoxy)aminobenzoate | 113010-52-9 |
| 8 | 2-Ethylhexyl 4-dimethylaminobenzoate | 21245-02-3 |
| 9 | 2-Ethylhexyl salicylate | 118-60-5 |
| 10 | 2-Isoamyl 4-methoxycinnamate | 71617-10-2 |
| 11 | 2-Ethylhexyl 4-methoxycinnamate | 5466-77-3 |
| 12 | 2-Hydroxy-4-methoxybenzophenone-5-sulfone (sulisobenzonone) and the sodium salt | 4065-45-6 |
| 13 | 3-(4'-Methyl)benzylidenebornan-2-one | 36861-47-9 |
| 14 | 3-Benzylidenebornan-2-one | 15087-24-8 |
| 15 | 1-(4'-Isopropylphenyl)-3-phenylpropane-1,3-dione | 63250-25-9 |
| 16 | 4-Isopropylbenzyl salicylate | 94134-93-7 |
| 17 | 3-Imidazol-4-ylacrylic acid and its ethyl ester | 104-98-3 |
| 18 | Ethyl 2-cyano-3,3-diphenylacrylate | 5232-99-5 |
| 19 | 2'-Ethylhexyl 2-cyano-3,3-diphenylacrylate | 6197-30-4 |
| 20 | Menthyl-o-aminobenzoate or: 5-methyl-2-(1-methylethyl)-2-aminobenzoate | 134-09-8 |
| 21 | Glyceryl p-aminobenzoate or: 1-glyceryl 4-aminobenzoate | 136-44-7 |
| 22 | 2,2'-Dihydroxy-4-methoxybenzophenone (dioxybenzone) | 131-53-3 |
| 23 | 2-Hydroxy-4-methoxy-4-methylbenzophenone (mexonone) | 1641-17-4 |
| 24 | Triethanolamine salicylate | 2174-16-5 |
| 25 | Dimethoxyphenylglyoxalic acid or: 3,4-dimethoxyphenylglyoxal acidic sodium | 4732-70-1 |
| 26 | 3-(4'-Sulfo)benzylidenebornan-2-one and its salts | 56039-58-8 |
| 27 | 4-tert-Butyl-4'-methoxydibenzoylmethane | 70356-09-1 |
| 28 | 2,2',4,4'-Tetrahydroxybenzophenone | 131-55-5 |
| 29 | Bis(2-ethylhexyl) 4,4'-[[6-[[4-[[(1,1-dimethyl-ethyl)-amino]carbonyl]phenyl]amino]-1,3,5-triazine-2,4-diyl]diimino]bisbenzoate | 154702-15-5 |
| 30 | 2-(2H-Benzotriazol-2-yl)-4-methyl-6-[2-methyl-3-[1,3,3,3-tetra-methyl-1-1[(trimethylsilyl)oxy]-disiloxanyl]propyl]phenol | 155633-54-8 |
| 31 | Dimethicone diethylbenzalmalonate | 207574-74-1 |
| 32 | Bis[2-hydroxy-5-tert-octyl-3-(benzotriazol-2-yl)phenyl]methane (bisoctyltriazone) | 103597-45-1 |
| 33 | 1H-Benzimidazole-4,6-disulfonic acid,2,2'-(1,4-phenylene)bis-,disodium salt (benzimidazylate) | 180898-37-7 |
| 34 | Phenol, 2,2'-[6-(4-methoxyphenyl)-1,3,5-triazine-2,4-diyl]bis[5-[(2-ethylhexyl)oxal]] (aniso triazine) | 187393-00-6 |

The cosmetic and dermatological preparations comprising photoprotective agents are usually based on a carrier which comprises at least one oil phase. Accordingly, oil, oil-in-water emulsions and water-in-oil emulsions, creams and pastes, lip protection stick masses or grease-free gels are suitable.

Such sunscreen preparations can, accordingly, be present in liquid, paste or solid form, for example as water-in-oil creams, oil-in-water creams and lotions, aerosol foam creams, gels, oils, grease sticks, powders, sprays or alcoholic-aqueous lotions.

Customary oil components in cosmetics are, for example, paraffin oil, glyceryl stearate, isopropyl myristate, diisopropyl adipate, cetylstearyl 2-ethylhexanoate, hydrogenated polyisobutene, vaseline, caprylic/capric triglycerides, microcrystalline wax, lanolin and stearic acid, and silicone oils.

Suitable silicone oils are, for example, linear polydimethylsiloxanes, poly(methylphenylsiloxanes), cyclic siloxanes and mixtures thereof. The number-average molecular weight of the polydimethylsiloxanes and poly(methylphenylsiloxanes) is preferably in a range from about 1000 to 150 000 g/mol. Preferably, cyclic siloxanes have 4- to 8-membered rings. Suitable cyclic siloxanes are commercially available, for example, under the name cyclomethicone.

PREPARATION EXAMPLE

An amphiphilic polymer was prepared by reacting $C_{13}$-oxo alcohol with 100 mol of butylene oxide/mole of C13-oxo alcohol in two stages and subsequent reaction with 164 mol of ethylene oxide/mole of C13-oxo alcohol, as described below:

Stage I Reaction of $C_{13}$-Oxo Alcohol with 22 Mol of Butylene Oxide/Mole of $C_{13}$-Oxo Alcohol 50 g of $C_{13}$-oxo alcohol and 0.9 g of potassium tert-butoxide were introduced into a 2 l metal reactor and then rendered inert three times using 5 bar of nitrogen in each case. The reactor contents were heated to 140° C., and then 396 g of butylene oxide were metered in. The mixture was then stirred to constant pressure. Following cooling and decompression of the reactor and the removal of gases on a rotary evaporator at 80° C. and 3 to mbar, 445.5 g of a $C_{13}$-oxo alcohol were obtained, which was alkoxylated with 22 equivalents of butylene oxide/mole.

Stage II Reaction of $C_{13}$-Oxo Alcohol with 78 Mol of Butylene Oxide/Mole of $C_{13}$-Oxo Alcohol 446 g of $C_{13}$-oxo alcohol butoxide from Stage I and 3.7 g of potassium tert-butoxide were introduced into a 3.5 l metal reactor and then rendered inert three times with 5 bar of nitrogen in each case. The reactor contents were heated to 140° C., and then 1404 g of butylene oxide were metered in. The mixture was then stirred to constant pressure. Following cooling and decompression of the reactor and removal of the gases on the rotary evaporator at 80° C. and 3 to 4 mbar, 1847.3 g of a $C_{13}$-oxo alcohol were obtained, which was alkoxylated with 100 equivalents of butylene oxide/mole.

Stage III Reaction of $C_{13}$-Oxo Alcohol Butoxide with 164 Mol of Ethylene Oxide/Mole of $C_{13}$-Oxo Alcohol 196 g of the $C_{13}$-oxo alcohol polybutoxylate from stage II and 0.9 g of potassium tert-butoxide were introduced into a 2 l metal reactor and then rendered inert three times with 5 bar of nitrogen in each case. The reactor contents were heated to 120° C., and then 190 g of ethylene oxide were metered in. The mixture was then stirred to constant pressure. Following cooling and decompression of the reactor and removal of the gases on a rotary evaporator at 80° C. and 3 to 4 mbar, a product with the following composition was obtained:

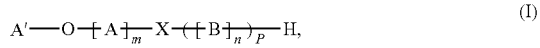

(I)

in which
A'-O is a $C_{13}$-oxo alcohol,
A is a structural unit of the formula

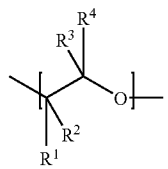

in which one of the radicals $R^1$ to $R^4$ is an ethyl radical and the other three radicals are hydrogen,
X is a structural unit of the formula

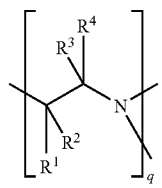

in which q=0 and
B is a monomeric subunit based on ethylene oxide.
OH number: 13 mg of KOH/g (theory: 10 mg of KOH/g)
Base number: 0.4 mg of KOH/g

APPLICATION EXAMPLE

The FIGURE below shows the shift in the X point, i.e. the minimum concentration of surfactant at a given temperature from which, for the reference system water/n-decane and a given surfactant (Lutensol® ON50 from BASF AG), the water and the n-decane phase are completely miscible and a thermodynamically stable microemulsion arises.

In the attached FIGURE, the concentration of the surfactant Lutensol® ON50, in the FIGURE as $c_{surfactant}$, is shown on the abscissa in % by weight, and the temperature in ° C. is shown on the ordinate. Sections from the respective phase diagrams ("Fisch" phase diagrams) are shown for the said water/n-decane 1:1 reference system, and said surfactant Lutensol® ON50 under I for comparison, i.e. without the addition of a cosurfactant, and under II for the application example according to the invention with the addition of the cosurfactant described above under the preparation example, in a concentration of 10%, based on the surfactant. The diagram shows that the X point of 22.5% of surfactant in the comparative example shifted to 15% surfactant in the example according to the invention with the addition of cosurfactant.

Application Examples of Cosmetic or Dermatological Preparations

For preparing cosmetic or dermatological preparations a cosurfactant was used which was obtained analogously to stage I from the above-described preparation example by reacting C13-oxo alcohol with 22 mol of butylene oxide/mol of C13-oxo alcohol and subsequent reaction analogous to stage III of the above preparation example, except with a total of 48 mol of alkylene oxide, of which 0.95% was ethylene oxide and 0.05% was propylene oxide. This amphiphilic polymer is referred to in the table below as cosurfactant*.

Emulsions for cosmetic or dermatological applications were prepared in accordance with the following general procedure:

The respective phases A (oil-containing) and B (aqueous) were heated separately to about 85° C. Phase A was stirred slowly and phase B was stirred into phase A, the mixing temperature being maintained above 80° C. With slow stirring, the mixture was cooled to room temperature.

The composition of phases A and B for example 1 is listed in the table below:

Example 1

| Phase | % by wt | INCI |
|---|---|---|
| A | 5.0 | Glyceryl stearate, ceteareth-20, ceteareth-12, cetearyl alcohol, cetyl palmitate |
|  | 1.0 | Ceteareth-20 |
|  | 5.0 | Caprylic/capric triglyceride |
|  | 5.0 | Mineral oil |
|  | 1.0 | Octyldodecanol |
|  | 1.0 | Ethylhexyl triazone (Uvinul ® T150) |
|  | 0.6 | Cosurfactant* |
| B | 5.0 | Glycerin |
|  | ad 100 | Aqua demin. |

This gave a microemulsion which was stable at room temperature, was sprayable and had a dynamic viscosity of less than 50 mPa·s.

Comparative Example 1

The amount of cosurfactant* was reduced to 0.4% by weight. No stable microemulsion was obtained.

Comparative Example 2

The amount of surfactant (the first two components of phase A in the table listed for Example 1) was reduced from 6% by weight to 4% by weight. No stable microemulsion was obtained.

We claim:

1. A mixture comprising a surfactant and a cosurfactant, wherein the cosurfactant is an amphiphilic polymer with the structure formula

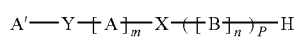  (I)

in which
A' is an unbranched or branched alkyl, cycloalkyl, aryl or aralkyl radical having 1 to 60 carbon atoms,
Y is S or O,
wherein A'-Y is a monofunctional unbranched or branched alcohol or thiol radical having 8 to 30 carbon atoms per molecule,
A is a structural unit with the formula

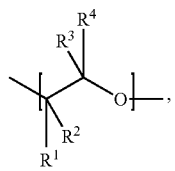

in which
$R^1$, $R^2$, $R^3$ and $R^4$ independently of one another, are the substituents hydrogen, methyl, ethyl, n-propyl, isopropyl, octyl or phenyl, with the restriction that at most three of the substituents $R^1$, $R^2$, $R^3$ and $R^4$ are hydrogen,
m is a number in the range from 10 to 300,
X is a structural unit with the formula

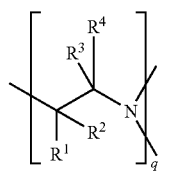

in which the substituents
$R^1$, $R^2$, $R^3$ and $R^4$ independently of one another, are each hydrogen, methyl, ethyl, n-propyl, isopropyl, octyl or phenyl,
q=1,
B is a monomeric subunit based on ethylene oxide or a mixture of ethylene oxide and propylene oxide,
n is a number in the range from 20 to 500 and
p=q+1.

2. The mixture as claimed in claim 1, wherein the structural unit A is formed from one or more of the monomers selected from the group consisting of propene oxide, 1-butene oxide, 2,3-butene oxide, 2-methyl-1,2-propene oxide (isobutene oxide), 1-pentene oxide, 2,3-pentene oxide, 2-methyl-1,2-butene oxide, 3-methyl-1,2-butene oxide, 2,3-hexene oxide, 3,4-hexene oxide, 2-methyl-1,2-pentene oxide, 2-ethyl-1,2-butene oxide, 3-methyl-1,2-pentene oxide, decene oxide, 4-methyl-1,2-pentene oxide, styrene oxide and a mixture of oxides of industrially available raffinate streams.

3. The mixture as claimed in claim 1, wherein the number m is a value in the range from 50 to 250.

4. The mixture as claimed in claim 1, wherein the number n is a value in the range between 50 and 300.

5. The mixture as claimed in claim 1, wherein B is an ethylene oxide/propylene oxide mixture containing 0 to 5000 of propylene oxide.

6. A process for the preparation of an amphiphilic polymer with the structural formula (I)

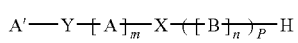  (I)

in which
A' is an unbranched or branched alkyl, cycloalkyl, aryl or aralkyl radical having 1 to 60 carbon atoms,
Y is S or O, wherein A'-Y is a monofunctional unbranched or branched alcohol or thiol radical having 8 to 30 carbon atoms per molecule, A is a structural unit with the formula

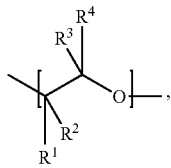

in which

R$^1$, R$^2$, R$^3$ and R$^4$ independently of one another, are the substituents hydrogen, methyl, ethyl, n-propyl, isopropyl, octyl or phenyl, with the restriction that at most three of the substituents R$^1$, R$^2$, R$^3$ and R$^4$ are hydrogen, m is a number in the range from 10 to 300;

X is a structural unit with the formula

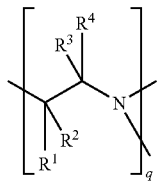

in which the substituents

R$^1$, R$^2$, R$^3$ and R$^4$ independently of one another, are each hydrogen, methyl, ethyl, n-propyl, isopropyl, octyl or phenyl, q=1, B is a monomeric subunit based on ethylene oxide or a mixture of ethylene oxide and propylene oxide, n is a number in the range from 20 to 500 and p=q+1, comprising reacting an unbranched or branched monohydroxyalkyl, -aryl or -aralkyl alcohol A'-OH or a corresponding thiol A'-SH with a monomer which forms the structural unit

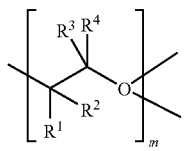

and reacting
  the terminal OH group directly with ethylene oxide or a mixture of ethylene oxide and propylene oxide or
  the terminal OH group firstly to give a primary or secondary amine and then with ethylene oxide or a mixture of ethylene oxide and propylene oxide.

7. A method for stabilizing an emulsion comprising adding the mixture as claimed in claim 1 to an emulsion.

8. A microemulsion comprising a surfactant and cosurfactant, wherein the cosurfactant is an amphiphilic polymer with the structural formula

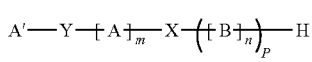 (I)

in which

A' is an unbranched or branched alkyl, cycloalkyl, aryl or aralkyl radical having 1 to 60 carbon atoms, Y is S or O, wherein A'-Y is a monofunctional unbranched or branched alcohol or thiol radical having 8 to 30 carbon atoms per molecule, A is a structural unit with the formula

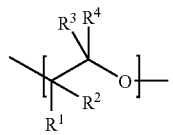

in which

R$^1$, R$^2$, R$^3$ and R$^4$ independently of one another, are the substituents hydrogen, methyl, ethyl, propyl, octyl or phenyl, with the restriction that at least two and at most three of the substituents R$^1$, R$^2$, R$^3$ and R$^4$ are hydrogen, m is a number in the range from 10 to 300, X is a structural unit with the formula

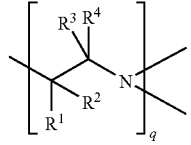

in which the substituents

R$^1$, R$^2$, R$^3$ and R$^4$ independently of one another, are the substituents hydrogen, methyl, ethyl, propyl, octyl or phenyl, q=1, B is a monomeric subunit based on ethylene oxide or a mixture of ethylene oxide and propylene oxide, n is a number in the range from 20 to 500 and p=q+1.

9. The microemulsion as claimed in claim 8, wherein A'-Y is a monofunctional unbranched or branched aliphatic alcohol or thiol radical having 8 to 30 carbon atoms per molecule.

10. The microemulsion as claimed in claim 8, wherein the structural unit A is formed from one or more monomers selected from the group consisting of propene oxide, 1-butene oxide, 2,3-butene oxide, 2-methyl-1,2-propene oxide (isobutene oxide), 1-pentene oxide, 2,3-pentene oxide, 2-methyl-1,2-butene oxide, 3-methyl-1,2-butene oxide, 2,3-hexene oxide, 3,4-hexene oxide, 2-methyl-1,2-pentene oxide, 2-ethyl-1,2-butene oxide, 3-methyl-1,2-pentene oxide, 4-methyl-1,2-pentene oxide, decene oxide, styrene oxide and a mixture of oxides of industrially available raffinate streams.

11. The microemulsion as claimed in claim 8, wherein the number m is a value in the range from 50 to 250.

12. The microemulsion as claimed in claim 8, wherein the number n is a value in the range between 50 and 300.

13. The microemulsion as claimed in claim 8, wherein B is an ethylene oxide/propylene oxide mixture containing 0 to 50% of propylene oxide.

14. A composition comprising the mixture as claimed in claim 1, wherein the composition is a detergent, an emulsifier, a foam regulator, a wetting agent for hard surfaces and a reaction medium for organic, inorganic, bioorganic or photochemical reactions.

15. A composition as claimed in claim 14, wherein the composition is utilized in detergents, surfactant formulations for the cleaning of hard surfaces, humectants, cosmetic, pharmaceutical and crop protection formulations, paints, coatings, adhesives, leather degreasing compositions, formulations for the textile industry, fiber processing, metal processing, food industry, water treatment, paper industry, fermentation, mineral processing, tire protection or in emulsion polymerizations.

16. A detergent, cleaner, wetting agent, coating, adhesive, leather degreasing composition, humectant or textile treatment composition or a pharmaceutical, crop protection or cosmetic formulation, sunscreen, skincare or hair styling composition, shower gel, shampoo, bath additive or scent oil, comprising a mixture as claimed in claim 1.

17. A detergent, cleaner, wetting agent, coating, adhesive, leather degreasing composition, humectant or textile treatment composition or a pharmaceutical, crop protection or cosmetic formulation, sunscreen, skincare or hair styling composition, shower gel, shampoo, bath additive or scent oil, comprising a microemulsion as claimed in claim 8.

18. A composition comprising a microemulsion as claimed in claim 8, wherein the composition is a detergent, an emulsifier, a foam regulator, a wetting agent for hard surfaces and a reaction medium for organic, inorganic, bioorganic or photochemical reactions.

19. A composition as claimed in claim 18, wherein the composition is utilized in detergents, surfactant formulations for the cleaning of hard surfaces, humectants, cosmetic, pharmaceutical and crop protection formulations, paints, coatings, adhesives, leather degreasing compositions, formulations for the textile industry, fiber processing, metal processing, food industry, water treatment, paper industry, fermentation, mineral processing, tire protection or in emulsion polymerizations.

* * * * *